United States Patent [19]
Doya et al.

[11] Patent Number: 5,440,004
[45] Date of Patent: Aug. 8, 1995

[54] METHOD AND APPARATUS FOR THE PRODUCTION OF ALKYLENE CARBONATE

[75] Inventors: Masaharu Doya; Yutaka Kanbara; Ken-ichi Kimizuka; Takashi Okawa, all of Niigata, Japan

[73] Assignee: Mitsubishi Gas Chemical Company, Inc., Tokyo, Japan

[21] Appl. No.: 238,743

[22] Filed: May 5, 1994

[30] Foreign Application Priority Data

May 19, 1993 [JP] Japan .................. 5-117202

[51] Int. Cl.$^6$ .............................. C08G 64/00
[52] U.S. Cl. ................... 528/196; 549/230; 549/229; 549/233; 549/518
[58] Field of Search ............. 528/196; 549/230, 229, 549/233, 518

[56] References Cited

U.S. PATENT DOCUMENTS 5,003,084  3/1991  Su et al. .................. 549/230

Primary Examiner—James J. Seidleck
Assistant Examiner—Terressa Mosley
Attorney, Agent, or Firm—Wenderoth, Lind & Ponack

[57] ABSTRACT

A method for the production of an alkylene carbonate at high yields and high selectivity by a reaction between an alkylene glycol and urea, the method being capable to preventing the deposition of a white crystal in the reflux condenser used in a conventional method for the production of alkylene carbonate and the subsequent decrease in the yield, wherein:

a gas washing member and a cooling member are disposed above a reaction portion where alkylene glycol and urea are allowed to react, ammonia-containing steam exhausted from the reaction portion is downwardly introduced into the cooling member through the gas washing member, condensate and ammonia gas exhausted from a bottom of the cooling member are gas-liquid separated, the condensate is introduced into the gas washing member, and the ammonia gas is removed from the reaction system.

5 Claims, 1 Drawing Sheet

METHOD AND APPARATUS FOR THE PRODUCTION OF ALKYLENE CARBONATE

FIELD OF THE INVENTION

The present invention relates to a method for the production of alkylene carbonate. Alkylene carbonate is important as an organic solvent, a processing agent for synthetic fibers, a raw material for a pharmaceutical composition or an intermediate for the synthesis of a dialkyl carbonate.

PRIOR ART OF THE INVENTION

Various methods are known for producing alkylene carbonate, while a method in which alkylene glycol and urea are allowed to react attracts attention. That is because the raw materials are available at relatively low costs and alkylene carbonate can be facilely produced. EP0443758A discloses a method in which alkylene glycol and urea are allowed to react under atmospheric pressure or elevated pressure in the absence of a catalyst or in the presence of a tin catalyst.

The reaction for producing alkylene carbonate from alkylene glycol and urea is represented by the following reaction scheme.

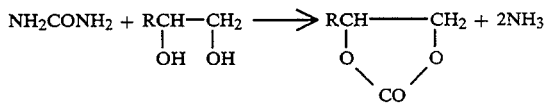

The above reaction is generally carried out by a method in which alkylene glycol is used in a greater molar ratio than that of urea, a reflux condenser is provided on the top of a reactor, and ammonia gas generated as a byproduct as the reaction proceeds is separated from the reaction system.

When the above reaction is carried out by the use of a reaction apparatus described above, however, a white crystal is deposited on the reflux condenser as the reaction proceeds, and the yield of alkylene carbonate calculated on the basis of urea decreases. When the above reaction is carried out by a batch method, the reflux condenser is rarely clogged since the period of time required for the reaction is not so long. In the continuous reaction, however, the amount of deposited crystal increases along with the operation of the apparatus, and the reflux condenser is finally clogged.

As a method for overcoming the above clogging phenomenon to proceed with the reaction smoothly, at least two series of reflux condensers may be provided so that these reflux condensers are switched as required. However, the switching operation is complicated, the apparatus requires an additional cost, and the above method cannot finally dissolve the decrease in the yield of alkylene carbonate.

SUMMARY OF THE INVENTION

It is an object of the present invention to provide a method for the production of alkylene carbonate from urea and alkylene glycol, in which the operation is facile, the yield is high and the selectivity to the alkylene carbonate is high.

It is another object of the present invention to provide a method for the production of alkylene carbonate, in which the deposition of a white crystal in the reflux condenser used in a conventional method for the production of alkylene carbonate can be prevented and the subsequent decrease in the yield can be therefore prevented.

It is further another object of the present invention to provide a method for the production of alkylene carbonate, in which the apparatus used therefor can be operated for a long period of time without clogging the apparatus.

According to the present invention, here is provided a method for the production of an alkylene carbonate by a reaction between an alkylene glycol and urea, wherein:

a gas washing member and a cooling member are disposed above a reaction portion where alkylene glycol and urea are allowed to react, ammonia-containing steam exhausted from the reaction portion is downwardly introduced into the cooling member through the gas washing member, condensate and ammonia gas exhausted from a bottom of the cooling member are gas-liquid separated, the condensate is introduced into the gas washing member, and the ammonia gas is removed from the reaction system.

DETAILED DESCRIPTION OF THE INVENTION

Figure 1:
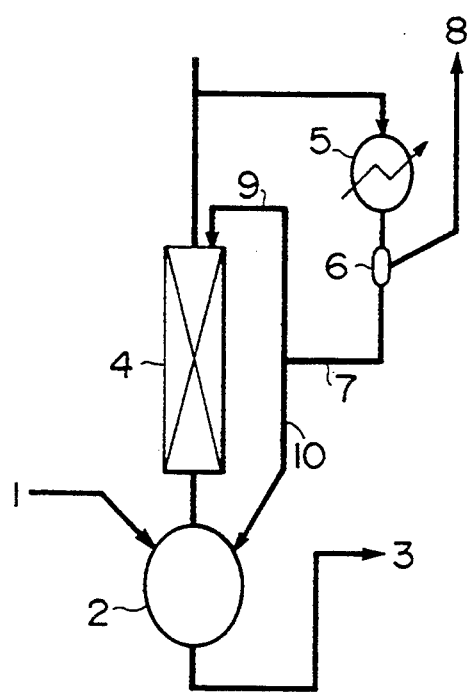
FIG. 1 is a flow chart showing the production of alkylene carbonate by the method according the present invention.

In the present invention, alkylene carbonate is produced by reacting alkylene with urea. The alkylene glycol has the general formula of $RCH(OH)CH_2OH$ in which R is hydrogen or a $C_1$-$C_4$ aliphatic alkyl group. The alkylene glycol includes, for example, ethylene glycol, 1,2-propylene glycol and 1,2-butylene glycol.

When the molar ratio of the alkylene glycol to urea is low, the urea itself undergoes a side reaction and the selectivity to alkylene carbonate decreases. Therefore, an excess amount of the alkylene glycol is allowed to react with urea, and generally the amount of the alkylene glycol per mole of urea is 1 to 5 mol.

In the present invention, the above reaction is carried out in the absence or presence of a catalyst, while it is preferred to use a catalyst containing zinc or magnesium for increasing the raction rate.

The amount of zinc or magnesium used as a catalyst is not specially limited, while the amount of zinc or magnesium metal per mole of urea is generally in the range of from 0.0001 to 10 mol, preferably 0.001 to 1 mol.

The reaction of the present invention is generally carried out in a system using an excess amount of alkylene glycol for increasing the selectivity to alkylene carbonate, and this reaction hence does not specially require the use of a solvent, while an inert solvent under the reaction conditions may be used.

The reaction of the present invention is carried out by mixing urea, the alkylene glycol and the optional catalyst, maintaining the mixture at a reaction temperature and at the same time removing formed ammonia from the reaction mixture. In the present invention, the reaction is carried out under the reflux of the alkylene glycol. The amount of the alkylene glycol under reflux is 1 to 100 mol per mole of ammonia which is formed.

In the present invention, the reaction temperature is preferably 120° to 200° C. When the reaction temperature is too low, the reaction rate is low. When it is too high, the amount of a by-product increases.

The reaction is carried out under atmospheric pressure or reduced pressure. Although differing depending upon the reaction liquid composition and reaction temperature, the pressure is generally in the range of from 60 mmHg to atmospheric pressure. The pressure reduction degree is properly selected so that the alkylene glycol is refluxed at a selected reaction temperature.

The reaction time differs depending upon the kind of the alkylene glycol, the molar ratio of the alkylene glycol to urea, the kind and amount of the catalyst, the reaction temperature and the amount of the alkylene glycol under reflux, while the reaction is generally carried out for 0.5 to 20 hours.

In the present invention, for bringing ammonia-containing steam exhausted from a reactor into contact with a condensate obtained by cooling the ammonia-containing steam, the reaction is carried out with an apparatus comprising a reaction portion, a gas washing member and a cooling member. Urea, the alkylene glycol and the optional catalyst are fed to the reaction portion, and the mixture is heated under atmospheric pressure or reduced pressure.

The above reaction portion is not specially structurally limited, while it is generally a reaction vessel with a stirrer.

The gas washing member has a structure in which the ammonia-containing steam exhausted from the reaction portion is brought into contact with a condensate formed by partial cooling or a condensate obtained by the gas-liquid separation of a fluid from the bottom of the cooling member. For example, a packed distillation column is used as the gas washing member.

The cooling member has a structure in which the ammonia-containing steam is fed from above and downwardly cooled for preventing the deposition of a crystallizable substance. The temperature in the outlet of the cooling member differs depending upon the pressure, and is not specially limited. Since, however, the amount of alkylene glycol which is entailed by the ammonia gas increases when the cooling temperature is high, it is generally set at 0° to 30° C.

The alkylene carbonate formed by the reaction is easily separated and recovered from the reaction mixture by a conventional method, e.g., by distillation.

The reaction in the present invention can be carried out any one of a batch method and a continuous method.

The present invention will be explained hereinafter with reference to drawings.

FIG. 1 shows the flow chart of one embodiment for producing an alkylene carbonate according to the method of the present invention.

A mixture containing urea, the alkylene glycol and the optional catalyst is introduced from a flow path 1 to a reaction portion 2. The reaction portion has a stirrer within it, and the reaction is carried out by externally heating the mixture. The alkylene carbonate formed by the reaction is separated through a flow path 3, the glycol which is entailing the alkylene carbonate is separated as required, and the alkylene carbonate is purified as required.

Ammonia-containing steam generated by the reaction is introduced into a gas washing member 4. The ammonia-containing steam from the gas washing member 4 is downwardly introduced to an upper portion of a cooling member, and a cooled fluid is separated into a condensate 7 and ammonia gas 8 with a gas-liquid separator 6. The condensate is composed mainly of unreacted alkylene glycol. The condensate is introduced into the gas washing member 4 through a flow path 9 to be brought into contact with the ammonia-containing steam, whereby a trace amount of a crystallizable substance contained in the ammonia-containing steam is dissolved in the condensate, and the deposition of a white crystal in the cooling member 5 can be prevented. The condensate may be introduced into the reaction portion 2 through a flow path 10.

EXAMPLES

The present invention will be detailed hereinafter with reference to Examples, while the present invention shall not be limited to these Examples.

The conversion of alkylene glycol in each of Examples and Comparative Examples is represented by the following equation. The conversion includes alkylene glycol which is entailed by formed ammonia and shows a value exceeding a theoretical value.

Conversion of alkylene glycol (%) = {(amount of fed alkylene glycol − amount of unreacted alkylene glycol) /amount of fed alkylene glycol} × 100.

Example 1

There was used an apparatus having a 500-ml three-necked flask equipped with a stirrer and a thermometer as the reaction portion shown in FIG. 1, a Snyder type fractional distillation tube as the gas washing member shown in FIG. 1 and a Liebig condenser as the cooling member shown in FIG. 1. The reaction portion was charged with 120.1 g (2.00 mol) of urea, 155.2 g (2.50 mol) of ethylene glycol and 6 g of zinc oxide, and while the mixture was stirred, the pressure in the reaction portion was reduced to 105 mmHg and the mixture was heated to 150° C. to carry out a batch reaction. The apparatus was arranged such that ammonia-containing steam exhausted from the reaction portion was cooled with the Liebig condenser and then an entire amount of a condensate was recycled to the Snyder type fractional distillation tube. After the reaction was carried out for 2 hours, the reaction mixture was cooled to give 212.8 g of a reaction liquid (including a condensate in a gas-liquid separator). The Liebig condenser and an exhaust gas line showed no deposition of a white crystal.

The reaction liquid was analyzed by gas chromatography to show that the content of unreacted ethylene glycol was 29.6 g and that the content of formed ethylene carbonate was 174.9 g.

The above results show that the conversion of ethylene glycol is theoretically 80.0% while it was 80.9%, that the selectivity to ethylene carbonate on the basis of reacted ethylene glycol was 98.3%, and that the selectivity to ethylene carbonate on the basis of urea was 99.3% (the conversion of urea was 100%).

Comparative Example 1

Figure 2:
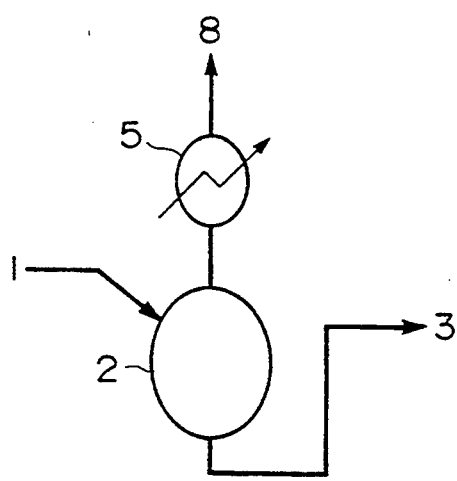
FIG. 2 is a flow chart showing a conventional method for the production of alkylene, in which a reflux condenser is disposed as part of the flow.

Example 1 was repeated except that the cooling member was replaced with a Dimroth condenser and that the condensate was directly recycled to the reactor without providing the gas washing member as shown in FIG. 2.

In addition, FIG. 2 shows the flow chart of a conventional method using a reflux condenser, and each numeral corresponds to a member indicated by such numeral in FIG. 1.

The same reaction as that in Example 1 was carried out and the reaction mixture was cooled to give 208.8 g of a reaction liquid. The Dimroth condenser had a large amount of a white crystal deposited therein.

The reaction liquid was analyzed by gas chromatography to show that the content of unreacted ethylene glycol was 38.7 g and that the content of formed ethylene carbonate was 162.0 g.

The above results show that the conversion of ethylene glycol is theoretically 80.0% while it was 75.1%, that the selectivity to ethylene carbonate on the basis of reacted ethylene glycol was 98.1%, and that the selectivity to ethylene carbonate on the basis of urea was 92.0% (the conversion of urea was 100%).

Example 2

The same apparatus as that used in Example 1 was used. The reaction portion was charged with 120.1 g (2.00 mol) of urea, 304.4 g (4.0 mol) of 1,2-propylene glycol and 1.5 g of magnesium oxide, and while the mixture was stirred, the mixture was heated to 190° C. under atmospheric pressure to carry out a batch reaction. The apparatus was arranged such that ammonia-containing steam exhausted from the reaction portion was cooled with the Liebig condenser and then an entire amount of a condensate was recycled to the Snyder type fractional distillation tube. After the reaction was carried out for 1 hour, the reaction mixture was cooled to give 355.9 g of a reaction liquid (including a condensate in a gas-liquid separator). The Liebig condenser and an exhaust gas line showed no deposition of a white crystal.

The reaction liquid was analyzed by gas chromatography to show that the content of unreacted 1,2-propylene glycol was 150.8 g and that the content of formed 1,2-propylene carbonate was 20.19 g.

The above results show that the conversion of 1,2-propylene glycol is theoretically 50.0% while it was 50.5%, that the selectivity to 1,2-propylene carbonate on the basis of 1,2-propylene glycol was 98.0%, and that the selectivity to 1,2-propylene carbonate the basis of urea was 98.9% (the conversion of urea was 100%).

Example 3

There was used an apparatus having a 500-ml three-necked flask equipped with a stirrer and a thermometer as the reaction portion shown in FIG. 1, a porcelain Raschig ring packed column as the gas washing member shown in FIG. 1 and a shell-and-tube condenser as the cooling member shown in FIG. 1. The reaction portion was fed with urea, 1,2-propylene glycol and zinc oxide in the urea:1,2-propylene glycol:zinc oxide amount ratio of 1 mol:2 mol:1.5 g to carry out a continuous reaction at a pressure reduction degree of 400 to 320 mmHg, at a reaction temperature of 170° C. for a residence time of 3 hours. Ammonia-containing steam exhausted from the reaction portion was passed through the Raschig ring packed column, then cooled with the shell-tube condenser, and gas-liquid separated. Part of the resultant condensate was directly recycled to the Raschig ring packed column, and part of the condensate was directly recycled to the reaction portion. After the reaction was continuously carried out for 30 hours, the shell-tube condenser and an exhaust gas line showed no deposition of a white crystal.

Part of the reaction product was weighed, and distilled to determine the yield to show that the conversion of 1,2-propylene glycol is theoretically 50.0% while it was 50.6%, that the selectivity to 1,2-propylene carbonate on the basis of reacted 1,2-propylene glycol was 98.3%, and that the selectivity to 1,2-propylene carbonate the basis of urea was 99.4% (the conversion of urea was 100%).

Comparative Example 2

Example 3 was repeated except that the apparatus was replaced with the apparatus described in Comparative Example 1 (FIG. 2). In this case, the Dimroth condenser was clogged 5 hours after the reaction started, and the experiment was terminated.

As explained above, the method of the present invention is free from the deposition of a white crystal in the cooling portion of the apparatus for the production of alkylene carbonate, and makes it possible to produce alkylene carbonate from urea and alkylene glycol at high yields and high selectivity. According to the present invention, therefore, alkylene carbonate can be industrially advantageously produced from less expensive urea and alkylene glycol.

What is claimed is:

1. A method for producing alkylene carbonate by reacting urea and alkylene glycol of the formula

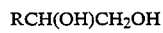

RCH(OH)CH$_2$OH where R is hydrogen or a C$_1$–C$_4$ aliphatic alkyl group, comprising:
   disposing a gas washing member and a cooling member above a reaction portion where urea and alkylene glycol, in excess relative to urea, are allowed to react under atmospheric pressure or reduced pressure at a temperature in the range of from 120 to 200° C.,
   washing ammonia-containing steam exhausted from the reaction portion with condensate obtained in the cooling member in the gas washing member and then downwardly introducing the washed ammonia-containing steam into the cooling member from above the cooling member,
   gas-liquid separating the condensate and ammonia gas exhausted from a bottom of the cooling member,
   introducing the condensate into the gas washing member, and
   removing the ammonia gas from the reaction system.

2. A method according to claim 1, wherein part of the condensate is introduced into the reaction portion.

3. A method according to claim 1, wherein the reaction between an alkylene glycol and urea is carried out using the alkylene glycol in an amount of 1 to 5 mol per mole of the urea.

4. A method according to claim 1, wherein gas washing is carried out using glycol in an amount of 1 to 100 mol per mole of ammonia which is formed.

5. A method according to claim 1, wherein the alkylene carbonate is exhausted from the reaction portion as a solution containing the alkylene carbonate and then recovered by distillation.

* * * * *

UNITED STATES PATENT AND TRADEMARK OFFICE
CERTIFICATE OF CORRECTION

PATENT NO.  :  5,440,004
DATED       :  August 8, 1995
INVENTOR(S) :  MASAHARU DOYA, YUTAKA KANBARA, KEN-ICHI KIMIZUKA and TAKASHI OKAWA It is certified that error appears in the above-indentified patent and that said Letters Patent is hereby corrected as shown below:

Claim 4  (column 6, line 62), insert "alkylene" before the word "glycol".

Signed and Sealed this

Twenty-second Day of October, 1996

BRUCE LEHMAN

*Attest:*

*Attesting Officer*    Commissioner of Patents and Trademarks